(12) United States Patent
Cifter et al.

(10) Patent No.: US 10,111,912 B2
(45) Date of Patent: Oct. 30, 2018

(54) HERBAL FORMULATIONS

(71) Applicant: MONTERO GIDA SANAYI VE TICARET A.S., Istanbul (TR)

(72) Inventors: Ümit Cifter, Istanbul (TR); Nazife Arabacioglu, Istanbul (TR); Özlem Toker, Istanbul (TR)

(73) Assignee: MONTERO GIDA SANAYI VE TICARET A.S., Istanbul (TR)

( * ) Notice: Subject to any disclaimer, the term of this patent is extended or adjusted under 35 U.S.C. 154(b) by 533 days.

(21) Appl. No.: 14/436,349

(22) PCT Filed: Oct. 17, 2013

(86) PCT No.: PCT/EP2013/071758
§ 371 (c)(1),
(2) Date: Apr. 16, 2015

(87) PCT Pub. No.: WO2014/060533
PCT Pub. Date: Apr. 24, 2014

(65) Prior Publication Data
US 2015/0290253 A1    Oct. 15, 2015

(30) Foreign Application Priority Data

Oct. 18, 2012 (TR) ............................ a 2012 12042
Oct. 18, 2012 (TR) ............................ a 2012 12043

(51) Int. Cl.
| | | |
|---|---|---|
| *A61K 36/258* | (2006.01) | |
| *A61K 36/9066* | (2006.01) | |
| *A61K 36/185* | (2006.01) | |
| *A61K 35/644* | (2015.01) | |
| *A61K 36/484* | (2006.01) | |
| *A61K 36/9068* | (2006.01) | |
| *A61K 36/61* | (2006.01) | |
| *A61K 35/63* | (2015.01) | |
| *A61K 9/00* | (2006.01) | |
| *A61K 47/12* | (2006.01) | |
| *A61K 47/26* | (2006.01) | |
| *A61K 47/46* | (2006.01) | |

(52) U.S. Cl.
CPC .......... *A61K 35/644* (2013.01); *A61K 9/0053* (2013.01); *A61K 9/0095* (2013.01); *A61K 35/63* (2015.01); *A61K 36/258* (2013.01); *A61K 36/484* (2013.01); *A61K 36/61* (2013.01); *A61K 36/9068* (2013.01); *A61K 47/12* (2013.01); *A61K 47/26* (2013.01); *A61K 47/46* (2013.01)

(58) Field of Classification Search
None
See application file for complete search history.

(56) References Cited

U.S. PATENT DOCUMENTS

| | | | | |
|---|---|---|---|---|
| 5,904,924 A | * | 5/1999 | Gaynor | A23L 33/175 424/195.17 |
| 8,653,135 B1 | * | 2/2014 | Dixit | A61K 45/06 514/561 |
| 2004/0126441 A1 | | 7/2004 | Pushpangadan et al. | |
| 2009/0155189 A1 | * | 6/2009 | Kovacs | A61K 9/006 424/48 |
| 2015/0273003 A1 | | 10/2015 | Cifter et al. | |
| 2015/0273009 A1 | | 10/2015 | Cifter et al. | |
| 2015/0290268 A1 | | 10/2015 | Cifter et al. | |

FOREIGN PATENT DOCUMENTS

| | | | |
|---|---|---|---|
| BE | 780165 A | * | 1/1972 |
| CH | 676931 A5 | | 3/1991 |
| CN | 10131893 A | * | 12/2008 |
| CN | 101637347 A | | 2/2010 |
| CN | 101695563 A | | 4/2010 |
| CN | 102100900 A | | 6/2011 |
| CN | 102258614 A | * | 11/2011 |
| CN | 102343077 A | | 2/2012 |
| CN | 102579916 A | * | 7/2012 |
| CN | 102698233 A | | 10/2012 |
| DE | 4211745 A1 | | 10/1993 |
| EP | 1520584 A1 | | 4/2005 |
| EP | 1829548 A1 | | 9/2007 |
| HU | 75540 T | * | 5/1997 |
| KR | 1041575 A | * | 6/2011 |
| RU | 2011106810 A | * | 8/2012 |
| WO | WO-2009/011498 A1 | | 1/2009 |
| WO | WO-2012/084075 A1 | | 6/2012 |
| WO | WO-2014/060525 A1 | | 4/2014 |
| WO | WO-2014/060529 A1 | | 4/2014 |

(Continued)

OTHER PUBLICATIONS

Aimbire et al., "Effect of hydroalcoholic extract of Zingiber officinalis rhizomes on LPS-induced rat airway hyperreactivity and lung inflammation," Prostaglandins Leukot Essent Fatty Acids. 77(3-4):129-38 (2007).

Cohen et al., "Effectiveness of an herbal preparation containing echinacea, propolis, and vitamin C in preventing respiratory tract infections in children: a randomized, double-blind, placebo-controlled, multicenter study," Arch Pediatr Adolesc Med. 158(3):217-21 (2004).

Fazio et al., "Tolerance, safety and efficacy of Hedera helix extract in inflammatory bronchial diseases under clinical practice conditions: a prospective, open, multicentre postmarketing study in 9657 patients," Phytomedicine. 16(1):17-24 (2009).

(Continued)

*Primary Examiner* — Christopher R Tate
*Assistant Examiner* — Randall Winston
(74) *Attorney, Agent, or Firm* — Kilpatrick Townsend & Stockton LLP

(57) ABSTRACT

The present invention relates to a formulation comprising *Propolis*, *Ginseng* root and *Zingiber officinale* extracts to be used in the treatment, prevention of various respiratory diseases or alleviation and/or elimination of symptoms thereof and a method for preparing said formulation.

18 Claims, No Drawings

(56) References Cited

FOREIGN PATENT DOCUMENTS

WO    WO-2014/060539 A1    4/2014

OTHER PUBLICATIONS

Hofmann et al., "Efficacy of dry extract of ivy leaves in children with bronchial asthma—a review of randomized controlled trials," Phytomedicine. 10(2-3):213-20 (2003).
International Preliminary Report on Patentability for PCT Application No. PCT/EP2013/071741, dated Apr. 21, 2015 (6 pages).
International Preliminary Report on Patentability for PCT Application No. PCT/EP2013/071750, dated Apr. 21, 2015 (7 pages).
International Preliminary Report on Patentability for PCT Application No. PCT/EP2013/071758, dated Apr. 21, 2015 (6 pages).
International Preliminary Report on Patentability for PCT Application No. PCT/EP2013/071766, dated Apr. 21, 2015 (6 pages).
International Search Report and Written Opinion for PCT Application No. PCT/EP2013/071741, dated Jan. 23, 2014 (9 pages).
International Search Report and Written Opinion for PCT Application No. PCT/EP2013/071750, dated Jan. 23, 2014 (11 pages).
International Search Report and Written Opinion for PCT Application No. PCT/EP2013/071758, dated Jan. 23, 2014 (9 pages).
International Search Report and Written Opinion for PCT Application No. PCT/EP2013/071766, dated Jan. 23, 2014 (10 pages).
Kemmerich et al., "Efficacy and tolerability of a fluid extract combination of thyme herb and ivy leaves and matched placebo in adults suffering from acute bronchitis with productive cough. A prospective, double-blind, placebo-controlled clinical trial," Arzneimittel Forschung./Drug Research. 56(9):652-60 (2006).
Matthys et al., "Efficacy and safety of an extract of Pelargonium sidoides (EPs 7630) in adults with acute bronchitis. A randomised, double-blind, placebo-controlled trial," Phytomedicine. 10(Suppl 4):7-17 (2003).
Matthys et al., "Pelargonium sidoides preparation (EPs 7630) in the treatment of acute bronchitis in adults and children," Phytomedicine. 14(Suppl 6):69-73 (2007).
Search Report and Written Opinion for Turkish Application No. TR201212043, dated Jul. 18, 2013 (18 pages).
Search Report and Written Opinion for Turkish Application No. TR201212044, dated May 14, 2013 (9 pages).
Database WPI; Week 201050; Thomson Scientific, London, GB; AN 2010-859696; XP002703289.
Database TCM [Online] SIPO; Apr. 21, 2010; Li Yongsheng: "Granule and powder for the prevention and treatment of chronic tracheitis and pulmonary heart disease." XP002703290.
Database WPI; Week 201304; Thomson Scientific, London, GB; AN 2013-A53251; XP002703291.

* cited by examiner

HERBAL FORMULATIONS

TECHNICAL FIELD

The present invention is related to a new formulation which comprises *Propolis* extract, *Ginseng* root extract and *Zingiber officinale* extract.

The present invention is also related to a method used for preparing a formulation comprising *Propolis* extract, *Ginseng* root extract and *Zingiber officinale* extract, as well as to the use of this formulation in the treatment and prevention of various respiratory tract diseases, or in the alleviation and/or elimination of the symptoms thereof in mammalians, particularly in humans.

BACKGROUND OF THE INVENTION

In recent years, the use of various herbs and/or herbal medical products for the prevention of disease, alleviating the effects thereof, or for treating diseases have been gradually increasing in all societies. Throughout the human history, there have been and still are attempts for treating many diseases (diabetes, jaundice, dyspnea, etc.) by using some herbs. According to the records of the World Heath Organization (WHO), a large proportion of the world's population (70-80%) makes use of herbs for therapeutic or prophylactic purposes. Additionally, around 25% of prescription drugs in developed countries are composed of plant based active agents (vinblastine, reserpine, quinine, aspirin, etc.) (Farnsworth et al., 1985).

Particularly following the end of the 1990s, the discovery of new areas of use for medical and aromatic herbs and the increasing demand for natural products have increased the use potential thereof day by day.

Herbal medical products have long been widely used for the treatment or prophylaxis of respiratory diseases. In the treatment or prophylaxis of these diseases which are typically caused by viruses, bacteria, and/or fungi, it is quite significant both to eradicate these harmful organisms and to boost the immune system of the affected individual. This is because the immune system is comprised of processes providing protection against diseases, as well as recognizing and eliminating the pathogenic and tumor cells in a living being. The system scans the organism against any kind of foreign substances, entering or contacting the former, from viruses to parasitic worms of a wide variety, and distinguishes them from the organism's own healthy cells and tissues.

The immune system can even distinguish substances with very similar features from each other to such an extent that even proteins having a different amino acid can be distinguished from the equivalents thereof. The function of the immune system is primarily to prevent harmful foreign substances from entering the respective organism, or upon entry, to retain the substances at the place of entry, or to prevent or delay their spreading therein.

*Propolis* is one of the most important bee products. Besides its antibacterial, antifungal, antiviral features, a great number of beneficial biological activities such as anti-inflammatory, anti-ulcer, local anesthetic, anti-tumor and immunity stimulant properties popularizes its usage in medicine, apitherapy, health nutrition and biocosmetic fields. It comprises 150 chemical compounds, more than 20 mineral substances, beeswax, resin and pollen. In chemical terms, *propolis* comprises a wide variety of extremely complex and potent terpenes, benzoic acids, caffeic acids, cinnamic acids, and phenolic acids. It has a high flavonoid content.

*Propolis* is one of the most powerful antibiotics found in nature. It is rich in terms of amino acids and trace metals, has a very high vitamin content and contains at least 38 valuable bioflavonoids. It is an invaluable antioxidant based on its high bioflavonoid content. It was demonstrated to inactivate at least 21 bacteria species, 9 fungi species, 3 protozoa (including *giardia*), and a wide spectrum of viruses.

In the studies, a lot of advantages of *propolis* for health are demonstrated. Some of these studies are: 1) A clinical study conducted in Spain in 1988 on 138 individuals has shown that the usage of a *propolis* based supplement is as effective as the usage of antiprotozoal drug tinidazole which is extensively used in the treatment of infections caused by giardiasis parasite. 2) A study published in *Nutrition and Cancer* in 2003 has shown that *propolis* has revitalized apoptosis and provided the tissue decomposition of the lung cancer tumors in mouse. 3) According to *National Institutes of Health*, *propolis* may be used as an effective anti-inflammatory agent against aphtha and other gingiva wounds and peptic ulcer. 4) *Blue Shield Complementary and Alternative Health* has reported that *propolis* is two times more effective than acyclovir which is the conventional anti-viral drug in herpes treatment. 5) According to a study published in *American Journal of Biochemistry and Biotechnology* on February 2004, *propolis* kills the human breast cancer cells called MCF-7. 13% of the cancer cells of the participants were killed only within 24 hours following the administration of *propolis* extract.

*Ginseng* root is harvested after a cultivation period of 6 years and this part of the plant is used for therapeutic purposes. It comprises saponins (dammaran and oleanan derivatives; ginsenosites), polyacetylene derivatives and polysaccharides. The effects of *Ginseng* on the body are not local, and thus, one of the benefits of *Ginseng* is that it strengthens the entire body and helps in balancing entire body systems. *Ginseng* is an antioxidant and an important immunity system improver which increases the number of immunity system cells in the body. It is useful in the treatment of bronchitis, asthma and circulation problems. According to a study conducted by American scientists, the flu risk of people who are administered 200 mg *ginseng* root capsules twice a day reduced by 31%. In the laboratory and animal experiments, it is found that it is effective against prostate, stomach, kidney, liver, large intestine, brain and lung cancers. In the animals with prostate cancer, it prevented the development of cancer.

Ginger (*Zingiber officinale*) is also called "warming herb" and used for a long time as an important medical herb. It comprises essential oils with ether comprising Zingiberene, Zingiberol, Gingerol and Shogol. The essential oils contained which are mixed with terpenoids give the special taste and scent of ginger. The bitter substances without essential oils which make the mouth feel warm are gingerol and zingeron.

Ginger has a wide area of usage. Ginger is preventive against cancer based on stopping the Epstein-barr virus activity. 6-gingerol and 6-paradol, among the active substances of ginger, are effective in stopping promyelocytic leucaemia by disturbing the DNA synthesis. It also has anti-inflammatory effect, is effective against arthritis and headache, and is bacteriostatic. It is used against nausea, spasm and fever in kids. Based on its antiseptic effect, it is used against stomach and intestine infections and even against food poisoning. It also prevents the coagulation of the blood and has blood thinning effect. It supports the cardiovascular system by making the platelets less adherent, this in turn causes a decrease in the problems of circulation system. It is appetizing and can also be used against constipation. In addition to these, it has a warming and sedative effect in cough, flu, cold and other respiratory system diseases.

Products to be used for medical purposes have to incorporate the elements of quality, efficiency, and reliability. A product can be a "medical" product only by having these elements. In order for the product prepared from a herbal source to be used in medicine, it has to be prepared from an effective and a standardized extract, pharmacological, clinical outcomes and toxicological data thereof has to be established as well as stability of the product has to be determined. Therefore, it bears great significance to have a good stability for a product, produced from herbal sources, to be used in the treatment and prevention of diseases, or in the alleviation and/or elimination of the symptoms thereof.

Physical, chemical and microbiological factors play role in the stability of drugs or other products manufactured for medical purposes. The stability issue is not dependent on a simple cause only, but emerges as a result of many factors. Factors such as the interaction of active agents contained in a product, the interaction of excipients among themselves or with active agents, pH, light, humidity, and temperature are among many factors which may influence the stability of such products.

Until recently, the researchers deemed considerable importance on the chemical stability of pharmaceutical products rather than the physical stability thereof and conducted many studies accordingly. In many instances, however, they could show how important the changes in the physical structures of products are for the product quality, and for the durability of the technologic, microbiologic, and biopharmaceutical properties thereof. Accordingly, it was shown that primarily the physical stability of a product has to be maintained in order to sustain its quality and other features thereof, and therefore ensuring the physical stability during the development of pharmaceutical products is as important as, or sometimes more important than ensuring the chemical stability thereof.

Additionally, the physical properties taken into account in the evaluation of the physical stability of a product, particularly the taste, scent, color, clarity, uniformity, etc. of a product, also considerably influence the patient compliance. For this reason, when a novel formulation is developed, besides aiming a formulation of good physical stability, the physical properties of this formulation should be made ideal to provide high patient compliance.

Having said that, it is quite difficult to ensure the requirements mentioned above in the formulations comprising herbal agents. Due to some characteristic chemical, biological, and physical properties of herbal agents incorporated in a formulation, some difficulties are experienced in obtaining a formulation comprising such substances, and having both good physical stability and ideal features in terms of patient compliance.

The physical properties and the physical stability of a formulation are influenced directly from the characteristic properties of herbal agents contained therein. Some aspects of herbal agents contained in a formulation, such as having a bad taste, a bad scent, a bad color and similar physical properties, becoming easily oxidized, and providing a suitable medium for the reproduction of microorganisms negatively influence the physical properties and physical stability of that formulation. Additionally, in case a formulation comprises a combination of herbal agents, a correct selection of the herbal agents bears great importance, since more than one herbal agent present in the same formulation are capable to mutually affect their respective properties.

Under the light of the foregoing, it would be desirable to provide a formulation, as well as a process for the preparation of this formulation, comprising combinations of herbal agents, being capable to retain the physical stability for a long time, and having ideal physical properties in terms of patient compliance.

In detail, there is a need in the state of art to a formulation comprising *Propolis* extract, *Ginseng* root extract and *Zingiber officinale* extract, and having ideal physical properties to ensure high patient compliance and good physical stability, as well as to a method for preparing this formulation, which is simple, cost-efficient and time-saving.

SUBJECT OF THE INVENTION

The main objective of the present invention is to provide a new formulation which comprises *Propolis* extract, *Ginseng* root extract and *Zingiber officinale* extract, overcomes the above mentioned problems and have advantages in comparison to the prior art formulations.

According to this main object, formulations according to the present invention are suitable for treatment, prevention of various respiratory diseases or alleviation and/or elimination of symptoms thereof.

Another object of the present invention is to provide a formulation comprising *Propolis* extract, *Ginseng* root extract, and *Zingiber officinale* extract with a good physical stability.

Another object of the present invention is to provide a formulation comprising *Propolis* extract, *Ginseng* root extract and *Zingiber officinale* extract, which both maintains the physical stability and has improved physical properties as a result of using suitable excipients.

Another object of the present invention is to provide a simple, cost effective and time saving process for the preparation of formulations comprising *Propolis* extract, *Ginseng* root extract and *Zingiber officinale* extract.

DESCRIPTION OF THE INVENTION

The maintenance of the physical stability of a pharmaceutical product can be ensured if no change occurs in the physical structure of that product. For this reason, the change in some physical properties of the product during a formulation development process is determined and it is assessed whether the physical stability is maintained. Properties such as the color, scent, taste, pH, clarity, viscosity, uniformity, density, etc. among the physical properties of a pharmaceutical product are the basic physical properties playing role in an evaluation of the physical stability of that product.

In the physical stability studies conducted during the development of a formulation comprising *Propolis* extract and *Ginseng* root extract for use in medicine, it was surprisingly found that adding extract of another herbal agent, namely *Zingiber officinale*, into the formulation, improved the physical stability of the product, and thus, the physical properties such as the color, scent, taste, pH, clarity, viscosity, uniformity, and the density thereof at the time the formulation was prepared were maintained for a longer time such that the physical stability was maintained as well.

In other words, it was found that the physical properties such as the color, scent, taste, density, clarity, homogeneity, viscosity, and the pH which are taken into account while the physical stability of a formulation comprising extracts of *Propolis, Ginseng* root (preferably *Panax ginseng*) ve *Zingiber officinale* is evaluated, remained unchanged for a longer time as compared to a formulation comprising extracts of *Propolis, Ginseng* root (preferably *Panax ginseng*) only.

When *Zingiber officinale* extract is added to the formulation which solely comprises *Propolis* extract and *Ginseng* root extract, the taste of the formulation worsens and changes to a strong bitter taste. Surprisingly, when more than 30% (w/v) of *Zingiber officinale* extract based on the total volume of formulation is added to the formulation comprising *Propolis* and *Ginseng* root extracts, it is found that the bad taste of the formulation can not be suppressed. This situation affects the patient compliance in a negative manner. However, when less than 30% (w/v) of *Zingiber officinale* extract based on the total volume of the formulation is added to the formulation according to the present invention, it is observed that the taste of the formulation can be enhanced.

Accordingly, the present invention, in more detail, is a formulation comprising *Propolis, Ginseng* root and *Zingiber officinale* extracts, wherein the percentage amount of the *Zingiber officinale* extract is less than 30% (w/v) based on the total volume of the formulation. In view of all the foregoing, the present invention provides a formulation which comprises *Propolis, Ginseng* root and *Zingiber officinale* extracts has both an enhanced taste for a high patient compliance and a good stability.

According to a preferred embodiment of the present invention, the percentage amount of the *Zingiber officinale* extract in the said formulation based on the volume of the total formulation is less than 15% (w/v) and more preferably between 0.2% and 5% (w/v), for example between 0.2% and 4.8%; between 0.2% and 4.5%; between 0.2% and 4.2%; between 0.2% and 4%; between 0.2% and 3.8%; between 0.2% and 3.5%; between 0.2% and 3.2%; between 0.2% and 3%; between 0.2% and 2.8; between 0.2% and 2.5%; between 0.2% and 2.2%; between 0.2% and 2%; between 0.2% and 1.8%; between 0.2% and 1.5%; between 0.2% and 1.2%; between 0.2% and 1%; between 0.3% and 4.8%; between 0.3% and 4.5%; between 0.3% and 4.2%; between 0.3% and 4%; between 0.3% and 3.8%; between 0.3% and 3.5%; between 0.3% and 3.2%; between 0.3% and 3%; between 0.3% and 2.8%; between 0.3% and 2.5%; between 0.3 and 2.2%; between 0.3% and 2%; between 0.3% and 1.8%; between 0.3% and 1.5%; between 0.3% and 1.2%; between 0.3% and 1%; between 0.4% and 4.8%; between 0.4% and 4.5%; between 0.4% and 4.2%; between 0.4% and 4%; 0.4% and 3.8%; between 0.4% and 3.5%; between 0.4% and 3.2%; between 0.4% and 3%; between 0.4% and 2.8%; between 0.4% and 2.5%; between 0.4% and 2.2%; between 0.4% and 2%; between 0.%4 and 1.8%; between 0.4% and 1.5%; between 0.4% and 1.2%; between 0.4% and 1%; between 0.5% and 4.8%; between 0.5% and 4.5%; between 0.5% and 4.2%; between 0.5% and 4%; between 0.5% and 3.8%; between 0.5% and 3.5%; between 0.5% and 3.2%; between 0.5% and 3%; between 0.5% and 2.8%; between 0.5% and 2.5%; between 0.5% and 2.2%; between 0.5% and 2%; between 0.5% and 1.8%; between 0.5% and 1.5%; between 0.5% and 1.2%; between 0.5% and 1%.

In another aspect of the present invention, it is found that adding *Glycyrrhiza glabra* extract to the formulation according to the invention comprising *Propolis, Ginseng* root and *Zingiber officinale* extracts enhances the taste of the formulation and improves the patient compliance. Thus, by adding *Glycyrrhiza glabra*, also known as Licorice, extract to the said formulation the taste of the said formulation is improved naturally and the usage amounts of the artificial sweeteners added to the formulation are minimized or the need for using an artificial sweetener in the formulation is eliminated. The percentage amount of the *Glycyrrhiza glabra* extract comprised in the formulation according to the present invention based on the total volume of the formulation is between 0.01% and 20% (w/v); preferably between 0.05% and 10% (w/v), and more preferably between 0.1% and 4% (w/v).

Licorice, *Glycyrrhiza glabra*, is a plant which is extensively used in respiratory and digestive system problems. Its pharmacologic effect is provided by substances contained in it such as glisirizin, coumarin, izoflavan, flamorait, saponin which are used in medical drugs. Besides that, in the content of licorice, substances such as carbendoxolane which treats ulcer, and flavonoids which are known for their powerful antioxidant features, are also present. Licorice is widely used in the medical drugs. Licorice has expectorant and diuretic features, reduces the harm of nicotine, cleans the bronchi, cures renal problems, passes the kidney and bladder stones and cures the ulcer lesions in the stomach.

Surprisingly, in the formulation according to the present invention, when *Glycyrrhiza glabra* extract and *Zingiber officinale* extract are used in a specific weight ratio, i.e. when the weight ratio of the *Glycyrrhiza glabra* extract to the *Zingiber officinale* extract is between 50:1 and 1:20, a synergistic effect on the physical stability of said formulation is observed in addition to that the taste of the formulation is improved. Thus, both a high patient compliance is provided by improving the taste of said formulation and maintenance of the quality, reliability and shelf life of the formulation having an improved physical stability is provided for longer periods.

Accordingly, in the formulation according to the present invention, the weight ratio of the *Glycyrrhiza glabra* extract to the *Zingiber officinale* extract is between 50:1 and 1:20, preferably between 30:1 and 1:10, and more preferably between 20:1 and 1:5.

In addition to this, the percentage amount of the *Propolis* extract present in the formulation according to the invention is between 0.02% and 30% (w/v); preferably between 0.02% and 15% (w/v) and more preferably between 0.02% and 5% (w/v) based on the total volume of the formulation whereas the percentage amount of the *Ginseng* root extract present in the formulation according to the invention is between 0.05% and 60% (w/v); preferably between 0.05% and 25% (w/v) and more preferably between 0.1% and 10% (w/v) based on the total volume of the formulation.

Within the scope of the present invention, the percentage amount of each herbal extract present in the formulation according to the invention is a gram-based amount of the respective herbal extract per 100 ml of the formulation.

In a further aspect, the formulation according to the present invention comprising the *Propolis* extract, the *Ginseng* root (preferably *Panax ginseng*) extract, the *Zingiber officinale* extract and the *Glycyrrhiza glabra* extract may be administered by oral, parenteral, ocular, nasal, buccal, sublingual, and topical route.

In a preferred embodiment of the present invention, the formulation is administered by oral route. However, infants, children, elders or patients having difficulty in swallowing can not easily use solid oral dosage forms. For this reason, in order to ensure high patient compliance and a successful treatment course, the formulation according to the present invention is preferably presented in a liquid oral dosage form and more preferably in the form of a syrup.

In a further aspect of the present invention, beside extracts of *Propolis*, *Ginseng* root, *Zingiber officinale* ve *Glycyrrhiza glabra* contained as active agents in said formulation, the formulation may further comprise the extracts of at least one of the following plants, which are known to be useful in the treatment, prevention of, or in the alleviation and/or elimination of the symptoms of various respiratory tract diseases and also in boosting the immune system: *Allium sativum, Juglans regia, Echinacea angustifolia, Echinacea atrorubens, Echinacea laevigata, Echinacea pallida, Echinacea paradoxa, Echinacea purpurea, Echinacea sanguinea, Echinacea simulata, Echinacea tennesseensis, Viola tricolor, Carduus marianus, Uncaria tomantosa, Codonopsis pilosula, Schisandra chinensis, Gynostemma pentaphyllum, Eleutherococcus senticosus, Pseudostellaria heterophylla, Withania somnifera, Pfaffia paniculata, Lepidium meyenii, Oplopanax horridus, Angelica sinensis, Pelargonium sidoides, Hedera helix, Panax notoginseng, Thymus citriodorus, Thymus herba-barona, Thymus pseudolanuginosus, Thymus serpyllum, Thymus vulgaris, Sambucus nigra, Tussilago farfara, Pimpinella anisum, Polypodium vulgare, Pinellia ternata, Citrus reticulata, Melissa officinalis, Primula veris, Lobelia* species, *Mullein* species, *Mentha piperita*.

Within the scope of the present invention, in addition to the extracts of *Propolis*, *Ginseng* root (preferably *Panax ginseng*), *Glycyrrhiza glabra* and *Zingiber officinale*, the said formulation also comprises more preferably at least one of the extracts of *Hedera helix, Pelargonium sidoides, Echinacea purpurea*.

In another aspect of the present invention, said formulation further comprises at least one excipient in addition to the herbal extracts mentioned above. Accordingly, the formulation according to the present invention further comprises at least one pharmaceutically acceptable excipient selected from the group comprising fillers, solvents, pH adjusting agents, sweeteners, aromatic agents and preservatives.

It is likely that the excipient or excipients comprised in the formulation may positively or adversely affect the characteristics, effectiveness and/or stability of the formulation by interacting with the herbal extracts and/or with each other. Therefore, when excipient selection is carried out for the formulation according to the present invention, the selection has to be made very carefully and object of the present invention must be considered.

Suitable fillers which may be contained in the formulation according to the present invention are selected from, the group comprising, but not limited to, sucrose, sorbitol, xylitol, dextrose, fructose, maltitol, sugar, potassium, aspartame, saccharine, saccharine sodium, spray dried or anhydrous lactose, mannitol, starch, cellulose (preferably, microcrystalline cellulose), and mixtures thereof; wherein the filler is preferably sorbitol.

Fillers are used as dispersion medium in the oral liquid formulations. In addition, they can also be used to adjust the concentration and to improve reproducibility of the formulation. These excipients are preferably used in solution form in the oral liquid formulations.

Sorbitol has some physical and chemical properties which makes it ideal for being used as a suitable filling agent in this invention. It is chemically inactive and thus, compatible with many excipients. At the same time, it dissolves easily in water and contributes to maintaining the stability of the formulation by increasing its viscosity. Besides all of the said features, sorbitol is also used as sweetener in pharmaceutical formulations.

In a formulation according to the present invention, it was found that when sorbitol was contained in an amount between 1% and 60% (w/v) based on the total volume of the formulation, it contributed both to improving the taste of the formulation, and to the prevention of crystallization thereof so that the homogeneity and the clarity of the formulation was maintained. The percentage amount of the sorbitol contained in the formulation according to the present invention based on the total volume of the formulation is preferably between 5% and 30% (w/v), and more preferably between 10% and 25% (w/v).

Suitable pH adjusting agents which may be contained in a formulation according to the present invention are selected from a group comprising, but not limited to, ascorbic acid, acetic acid, tartaric acid, citric acid, sodium citrate, potassium citrate, sodium phosphate, tricalcium phosphate, calcium carbonate, sodium bicarbonate, calcium phosphates, carbonated calcium phosphates, magnesium hydroxide and the hydrates thereof and the mixtures thereof, wherein the pH adjusting agents are preferably citric acid monohydrate and sodium citrate dihydrate.

According to the present invention, it was observed that setting the weight ratio of sodium citrate dihydrate to citric acid monohydrate contained in said formulation at 1:2 and thus keeping the pH at an acidic level contributed to improving the taste of the formulation and to maintaining the physical stability of the formulation, based on a constant pH. The percentage amount of citric acid monohydrate in said formulation is between 0.01% and 1% (w/v), preferably between 0.02% and 0.5% (w/v), more preferably between 0.03% and 0.2% (w/v) based on the total volume of the formulation, whereas the percentage amount of sodium citrate dihydrate is between 0.005% and 0.5% (w/v), preferably between 0.01% and 0.25% (w/v), and more preferably between 0.015% and 0.1% (w/v) on the same basis. The pH of the formulation according to the present invention is between 2 and 6.5, preferably between 3 and 6, and more preferably between 3.5 and 5.5.

Suitable preservatives which may be contained in a formulation according to the present invention are selected from a group comprising, but not limited to, methylparaben and propylparaben and the salts thereof (e.g. sodium, potassium), sodium benzoate, citric acid, benzoic acid, butylated hydroxytoluene and butylated hydroxyanisole, and the mixtures thereof.

Here, it was surprisingly found that when the above indicated percentages of herbal extracts were added to a formulation according to the present invention, the need to include a preservative in said formulation was avoided due to the characteristic features of these extracts, particularly the antibacterial, antiviral, and/or antioxidative features of the same.

Thus, when a formulation according to the present invention contains the above indicated percentages of herbal extracts, the physical stability thereof can be maintained for a longer time without containing a preservative and a more natural formulation can be obtained as compared to the formulation comprising a preservative.

Suitable aromatic agents which may be contained in a formulation according to the present invention are selected from a group comprising, but not limited to, fruit aromas like of orange, cherry, strawberry, banana, sourcherry, lemon; aromas of cardamom, anis, mint, menthol, *eucalyptus*, vanillin, and ethyl vanillin and the mixtures thereof, wherein the aromatic agent is preferably *eucalyptus*.

When *eucalyptus* was used as an aromatic agent as said above, it was observed that *eucalyptus* provided a supportive effect on the action of the formulation based on the refreshing and smoothening effects of *eucalyptus* scent, and that patients receiving this formulations experienced an instant relief as well as an alleviation in the symptoms, and thus it helped them to feel better in a relatively short time. Based on said effect of a formulation according to the present invention comprising *eucalyptus* as an aromatic agent, it was further observed that the formulation increased patient compliance and that the process in which the patients using this formulation complied with the treatment was accelerated. The percentage amount of *eucalyptus* used as an aromatic agent according to the present invention is between 0.01% and 5% (w/v), preferably between 0.03% and 3% (w/v), and more preferably between 0.05% and 2% (w/v), based on the total volume of the formulation.

Suitable sweeteners which may be contained in a formulation according to the present invention are selected from a group comprising, but not limited to, sucralose, ammonium glycyrrhizinate, acesulfame-K, aspartame, saccharine or sodium and calcium salts of saccharine, sodium cyclamate, sucrose, fructose, glucose, sorbitol and the mixtures thereof. The percentage amount of a sweetener contained in a formulation according to the present invention is between 0.005% and 20% (w/v), preferably between 0.005% and 15% (w/v) and more preferably between 0.005% and 10% (w/v), based on the total volume of the formulation.

Suitable solvents which may be contained in a formulation according to the present invention are selected from a group comprising, but not limited to, propylene glycol, glycerin, water, ethanol, isopropyl alcohol and similar water-soluble polar and water-insoluble non-polar solvents, or the mixture thereof. In order to prepare a formulation according to the present invention in an ideal manner, at least 5% and preferably at least 15% thereof has to be comprised of a solvent.

The formulation according to the present invention can be used as a pharmaceutical and/or phytotherapeutic formulation and also as a food supplement.

According to the present invention, all herbal extracts contained in the formulation can be obtained from the shelf, leaf, flower, root or from the seed thereof.

All extracts according to the present invention are obtained by using methods of the prior art.

In another aspect, the present invention provides a formulation used for the treatment, prevention of, and/or for the alleviation of the effects of parasitic diseases, skin diseases, acute and chronic respiratory tract infections, cold, pharyngitis, angina, sinusitis, acute bronchitis, tonsillitis, bronchial asthma, chronic obstructive pulmonary disease, acute and chronic airway inflammation, lower and upper respiratory tract infections, acute and chronic inflammatory bronchial diseases, infections of the ear, nose, and throat, other bacterial and viral respiratory tract diseases. Additionally, the formulation according to the present invention can be used in the alleviation and/or elimination of the symptoms resulting from said diseases, in boosting the immune system, as well as be used as an expectorant, an anti-inflammatory agent, antibacterial agent and antiviral agent, and in alleviating the symptoms like cough and the sore throat.

A formulation according to the present invention comprising herbal substances, having improved physical stability, being preferably in the liquid oral dosage form comprises:
 a. 0.02% to 30% by weight of *Propolis* extract,
 b. 0.05% to 60% by weight of *Ginseng* root extract,
 c. 0.05% to 30% by weight of *Zingiber officinale* extract,
 d. 1% to 60% by weight of propylene glycol,
 e. 25% to 50% by weight of glycerin,
 f. 0.01% to 1% by weight of citric acid monohydrate,
 g. 0.005% to 0.5% by weight sodium citrate dihydrate,
 h. 1% to 60% by weight of sorbitol,
 i. 0.01% to 2% by weight of sucralose,
 j. 0.01% to 10% by weight of ammonium glycerizinate,
 k. 0.5% to 30% by weight of ethanol,
 l. 0.01% to 5% by weight of *eucalyptus*,
 m. sufficient amount of water until the total volume is 100 ml.

In a preferred embodiment of the present invention, above mentioned formulation according to the present invention comprises:
 a. 0.02% to 30% by weight of *Propolis* extract,
 b. 0.05% to 60% by weight of *Ginseng* root extract,
 c. 0.05% to 30% by weight of *Zingiber officinale* extract,
 d. 0.01% to 20% by weight of *Glycyrrhiza glabra* extract,
 e. 1% to 60% by weight of propylene glycol,
 f. 25% to 50% by weight of glycerin,
 g. 0.01% to 1% by weight of citric acid monohydrate,
 h. 0.005% to 0.5% by weight sodium citrate dihydrate,
 i. 1% to 60% by weight of sorbitol,
 j. 0.01% to 2% by weight of sucralose,
 k. 0.01% to 10% by weight of ammonium glycerizinate,
 l. 0.5% to 30% by weight of ethanol,
 m. 0.01% to 5% by weight of *eucalyptus*,
 n. sufficient amount of water until the total volume is 100 ml.

In a preferred embodiment of the present invention, above mentioned formulation according to the present invention comprises:
 a. 0.02% to 15% by weight of *Propolis* extract,
 b. 0.05% to 25% by weight of *Ginseng* root extract,
 c. 0.1% to 15% by weight of *Zingiber officinale* extract,
 d. 1% to 60% by weight of propylene glycol,
 e. 25% to 50% by weight of glycerin,
 f. 0.02% to 0.5% by weight of citric acid monohydrate,
 g. 0.01% to 0.25% by weight sodium citrate dihydrate,
 h. 5% to 30% by weight of sorbitol,
 i. 0.01% to 2% by weight of sucralose,
 j. 0.01% to 10% by weight of ammonium glycerizinate,
 k. 0.5% to 30% by weight of ethanol,
 l. 0.03% to 3% by weight of *eucalyptus*,
 m. sufficient amount of water until the total volume is 100 ml.

In a preferred embodiment of the present invention, above mentioned formulation according to the present invention comprises:
 a. 0.02% to 15% by weight of *Propolis* extract,
 b. 0.05% to 25% by weight of *Ginseng* root extract,
 c. 0.1% to 15% by weight of *Zingiber officinale* extract,
 d. 0.05% to 10% by weight of *Glycyrrhiza glabra* extract,
 e. 1% to 60% by weight of propylene glycol,
 f. 25% to 50% by weight of glycerin,
 g. 0.02% to 0.5% by weight of citric acid monohydrate,
 h. 0.01% to 0.25% by weight sodium citrate dihydrate,
 i. 5% to 30% by weight of sorbitol,
 j. 0.01% to 2% by weight of sucralose,
 k. 0.01% to 10% by weight of ammonium glycerizinate,
 l. 0.5% to 30% by weight of ethanol,
 m. 0.03% to 3% by weight of *eucalyptus*,
 n. sufficient amount of water until the total volume is 100 ml.

In a preferred embodiment of the present invention, above mentioned formulation according to the present invention comprises:

a. 0.02% to 5% by weight of *Propolis* extract,
b. 0.1% to 10% by weight of *Ginseng* root extract,
c. 0.2% to 5% by weight of *Zingiber officinale* extract,
d. 1% to 60% by weight of propylene glycol,
e. 25% to 50% by weight of glycerin,
f. 0.03% to 0.2% by weight of citric acid monohydrate,
g. 0.015% to 0.1% by weight of sodium citrate dihydrate,
h. 10% to 25% by weight of sorbitol,
i. 0.01% to 2% by weight of sucralose,
j. 0.01% to 10% by weight of ammonium glycerizinate,
k. 0.5% to 30% by weight of ethanol,
l. 0.05% to 2% by weight of *eucalyptus,*
m. sufficient amount of water until the total volume is 100 ml.

In a preferred embodiment of the present invention, above mentioned formulation according to the present invention comprises:
a. 0.02% to 5% by weight of *Propolis* extract,
b. 0.1% to 10% by weight of *Ginseng* root extract,
c. 0.2% to 5% by weight of *Zingiber officinale* extract,
d. 0.1% to 4% by weight of *Glycyrrhiza glabra* extract,
e. 1% to 60% by weight of propylene glycol,
f. 25% to 50% by weight of glycerin,
g. 0.03% to 0.2% by weight of citric acid monohydrate,
h. 0.015% to 0.1% by weight sodium citrate dihydrate,
i. 10% to 25% by weight of sorbitol,
j. 0.01% to 2% by weight of sucralose,
k. 0.01% to 10% by weight of ammonium glycerizinate,
l. 0.5% to 30% by weight of ethanol,
m. 0.05% to 2% by weight of *eucalyptus,*
n. sufficient amount of water until the total volume is 100 ml.

Within the scope of the present invention, the percentage amounts of substances by weight contained in the formulation represent the gram amounts provided in the 100 ml formulation.

According to another object of the present invention, the preferred process according to the present invention for preparing the formulation comprises the following steps:
a. all solvents are added to the manufacturing vessel and mixed until a homogeneous mixture is obtained (mixture A),
b. inactive ingredients are added to the vessel containing mixture A and mixed until a homogeneous mixture is obtained (mixture B),
c. herbal substance extracts are added onto the mixture B obtained in the previous step successively and mixed until a homogeneous mixture is obtained (mixture C),
d. the obtained mixture C is converted into suitable dosage forms and filled into the packages.

Another preferred process for preparing formulation being preferably in liquid oral dosage form according to the present invention comprises the following steps:
a. all solvents are added to the manufacturing vessel and mixed until a homogeneous mixture is obtained (mixture A),
b. inactive ingredients are added to the vessel containing mixture A and mixed until a homogeneous mixture is obtained (mixture B),
c. herbal substance extracts are added onto the mixture B obtained in the previous step successively and mixed until a homogeneous mixture is obtained (mixture C),
d. obtained mixture C is subjected to filtration process and let to settle,
e. at the end of the settling period the obtained final product is filled into suitable bottles.

During the manufacturing processes described above, homogenizer and mixer are run at high speeds and mixing process is continued until a homogeneous mixture which is free of solid masses is obtained.

Experimental Studies for Evaluation of the Physical Stability

On the purpose of demonstrating stability of the formulation to be improved when it contains the combination of *Propolis* extract, *Ginseng* root extract and *Zingiber officinale* extract, firstly, five formulations are prepared according to the present invention. These formulations comprise:

Formulation 1: *Propolis* extract+excipients
Formulation 2: *Ginseng* root extract+excipients
Formulation 3: *Zingiber officinale*+excipients
Formulation 4: *Propolis* extract & *Ginseng* root extract+excipient
Formulation 5: *Propolis* extract & *Ginseng* root extract & *Zingiber officinale*+excipients Each of the above formulations prepared for the comparative experimental analysis comprises same excipients in the same amounts.

Examining changes in physical properties such as pH, density, viscosity, color, precipitation, taste, smell, etc of the formulations under stress conditions is useful in evaluating the physical stability of the formulations. Therefore, stress testing is carried out on the above formulations in an drying-oven at the temperature of 50° C. as a thermal condition and under conditions defined in *ICH Q1B Photostability Testing of New Drug Substances and Products* to determine the physical changes of the formulations. At specific time periods, physical analyses of the formulations are performed. Suprisingly, it has found that the formulation comprising the combination of *Propolis* extract, *Ginseng* root extract and *Zingiber officinale* extract is the most stable formulation among the formulations that are analysed. Comparative results obtained at the end of the stress testing are given below:

Thermal Stress Testing

Thermal stress testing is carried out on the above formulations that are kept in a drying-oven with the temperature of 50° C. throughout 10 days. During testing period, the changes in the physical properties of the formulations are determined, and comparative results obtained at the end of the testing period are given below.

pH

According to the comparative results of Table 1, the change in pH value of the Formulation 1, 2, 3, and 4 is higher than that of the Formulation 5 throughout the testing period. Although the change in pH values of the formulations comprising *Propolis, Ginseng* root or *Zingiber officinale* is higher than the formulations comprising double combination (Formulation 4) or triple combination (Formulation 5), in fact, the pH values of the Formulation 5 remains almost the same throughout the testing period. It shows that the formulation comprising the combination of *Propolis, Ginseng* root and *Zingiber officinale* is most stable formulation among the other formulations with regard to the change in pH values. Suprisingly, it has also found that while the pH value of the formulation approaches to 4, the taste of the formulation becomes better, thus, the Formulation 3 has the best taste among the formulations.

The increase occurred in the pH values of the Formulation 1-4 also leads to the taste of the formulations to be changed throughout the testing period.

TABLE 1 pH values in the formulations versus time

|   | 0 h | 5 h | 21 h | 29 h | 44 h | 54 h | 5 d | 6 d | 8 d | 9 d | 10 d |
|---|---|---|---|---|---|---|---|---|---|---|---|
| Formulation 1 | 3.81 | 3.95 | 3.97 | 3.96 | 4.02 | 4.08 | 4.06 | 4.05 | 4.09 | 4.13 | 4.19 |
| Formulation 2 | 4.30 | 4.37 | 4.43 | 4.51 | 4.49 | 4.53 | 4.55 | 4.59 | 4.67 | 4.66 | 4.69 |
| Formulation 3 | 4.69 | 4.75 | 4.73 | 4.82 | 4.95 | 5.03 | 4.97 | 4.99 | 5.04 | 5.02 | 5.06 |
| Formulation 4 | 4.05 | 4.12 | 4.09 | 4.13 | 4.12 | 4.17 | 4.21 | 4.20 | 4.24 | 4.22 | 4.26 |
| Formulation 5 | 4.04 | 4.00 | 4.02 | 4.01 | 4.02 | 4.02 | 4.02 | 4.00 | 4.02 | 4.00 | 4.03 | h: hour;
d: day

The pH values of the formulations throughout the testing period are measured using Mettler Toledo/Seven Multi pH meter at room tempereture (25° C.±2° C.)

Density

According to the comparative results of Table 2, the increase in density of the Formulation 1, 2, 3, and 4 is higher than that of the Formulation 5 throughout the testing period. As the same in the density of the formulations, the increase in the viscosity of the Formulation 1, 2, 3 and 4 is higher than that of the Formulation 5 throughout the testing period that is shown in Table 3.

TABLE 2

Densities of the formulations versus time

|   | 0 d | 10 d |
|---|---|---|
| Formulation 1 | 1.1297 g/mL | 1.1575 g/mL |
| Formulation 2 | 1.1321 g/mL | 1.1571 g/mL |
| Formulation 3 | 1.1274 g/mL | 1.1447 g/mL |
| Formulation 4 | 1.1316 g/mL | 1.1452 g/mL |
| Formulation 5 | 1.1342 g/mL | 1.1350 g/mL | d: day

TABLE 3

Viscosities of the formulations versus time

|   | 0 d | 10 d |
|---|---|---|
| Formulation 1 | 18.5 mP | 21.8 mP |
| Formulation 2 | 19.8 mP | 21.7 mP |
| Formulation 3 | 18.2 mP | 21.4 mP |
| Formulation 4 | 19.2 mP | 21.5 mP |
| Formulation 5 | 20.6 mP | 20.7 mP | d: day

The densities of the formulations throughout the testing period are measured using Mettler Toledo DE40 density meter at room temperature (25° C.±2° C.) and the viscosities of the formulations throughout the testing period are measured using BROOKFIELD DV-II+Pro viscosity meter at room temperature (25° C.±2° C.).

Precipitation

As shown in Table 4, although the precipitation is observed in the formulation comprising *Propolis* alone (Formulation 1) and in the formulation comprising *Zingiber officinale* alone (Formulation 3), any precipitation is not observed when *Propolis* & *Ginseng* root or *Propolis* & *Ginseng* root & *Zingiber officinale* present together in the formulation (Formulation 4 or Formulation 5 respectively). Additionally, the formulations in which any precipitation is not observed have a clear appearance and maintain this clarity throughout the testing period.

TABLE 4

Precipitation in the formulations versus time

|   | 0 h | 5 h | 21 h | 29 h | 44 h | 54 h | 5 d | 6 d | 8 d | 9 d | 10 d |
|---|---|---|---|---|---|---|---|---|---|---|---|
| Formulation 1 | + | + | + | + | + | + | + | + | + | + | + |
| Formulation 2 | − | − | − | − | − | − | − | − | − | − | − |
| Formulation 3 | + | + | + | + | + | + | + | + | + | + | + |
| Formulation 4 | − | − | − | − | − | − | − | − | − | − | − |
| Formulation 5 | − | − | − | − | − | − | − | − | − | − | − | h: hour;
d: day

This physical analysis to determine whether the precipitation is occured or not in the formulations throughout the testing period, is performed by same analyst. Additionally, the analysis of each formulation is performed on the same ground which is a white flat ground lightened with a flash light parallel to the ground.

Color

As shown in Table 5, although the color change is observed in the formulation comprising the combination of *Propolis* and *Ginseng* root (Formulation 4), any color change is not observed in the formulation comprising the combination of *Propolis*, *Ginseng* root and *Zingiber officinale* (Formulation 5) throughout the testing period. Additionally, except for the Formulation 2, the other formulations comprising single extract undergo to the color change throughout the testing period.

TABLE 5

Color change in the formulations versus time

| | 0 s | 5 s | 21 s | 29 s | 44 s | 54 s | 5 d | 6 d | 8 d | 9 d | 10 d |
|---|---|---|---|---|---|---|---|---|---|---|---|
| Formulation 1 | light brown | light brown | light brown | yellow | yellow | yellow | light yellow | light yellow | light yellow | light yellow | light yellow |
| Formulation 2 | light yellow | light yellow | light yellow | light yellow | light yellow | light yellow | light yellow | light yellow | light yellow | light yellow | light yellow |
| Formulation 3 | light brown | light brown | yellow | yellow | light yellow | light yellow | light yellow | light yellow | light yellow | light yellow | light yellow |
| Formulation 4 | light brown | light brown | light brown | yellow | yellow | yellow | yellow | yellow | yellow | yellow | yellow |
| Formulation 5 | light brown | light brown | light brown | light brown | light brown | light brown | light brown | light brown | light brown | light brown | light brown | h: hour;
d: day

This physical analysis to determine whether the precipitation is occured or not in the formulations throughout the testing period, is performed by same analyst. Additionally, the analysis of each formulation is performed on the same ground which is a white flat ground lightened with a flash light parallel to the ground, and the color of the formulations is decided using a color scale.

Smell

It is observed that the smell of the Formulation 5 does not change whereas the smell of the other formulations change throughout the testing period. This physical analysis is also performed by same analyst in the same odorless environment for each formulation.

According to the thermal stress testing results, although the temperature at which the physical analyses are performed is high (50° C.), the Formulation 5 is less affected from the temperature in comparison with the other formulations, and thus, the physical stability of the Formulation 3 remains stable throughout the testing period.

Photostability Stress Testing

For determining the photostability of the formulations, the photostability stress testing is carried out under conditions defined in *ICH Q1B Photostability Testing of New Drug Substances and Products*. Two different conditions defined in the guideline are used during the testing period: initially formulations are kept in a photostability cabine with 200 Wh/m² at a constant temperature (25° C.) during 4 hours (ICH parameter-1). After the physical analyses of the formulations are carried out, these formulations are kept in a photostability cabine with 1.2 million lux hours at a constant temperature (25° C.) during 10 hours (ICH parameter-1).

According to the comparative results shown in Table 6, the Formulation 5 is the most photostable formulation among the formulations. The Formulation 5 is less affected from the light stress in comparison with other formulations, and thus, the change in the physical properties of the Formulation 5 is less than that of the Formulation 1, 2, 3, and 4 at the end of the testing periods.

TABLE 6

Photostability of the formulations

| | ICH parameter -1 | | | | ICH parameter -2 | | | |
|---|---|---|---|---|---|---|---|---|
| | pH | Density (g/mL) | Precipitation | Color | pH | Density (g/mL) | Precipitation | Color |
| Formulation 1 | 3.97 | 1.1299 | + | yellow | 4.18 | 1.1325 | + | light yellow |
| Formulation 2 | 4.47 | 1.1322 | − | light yellow | 4.62 | 1.1398 | − | light yellow |
| Formulation 3 | 4.88 | 1.1276 | + | yellow | 5.01 | 1.1352 | + | yellow |
| Formulation 4 | 4.07 | 1.1334 | − | light brown | 4.19 | 1.1402 | − | light brown |
| Formulation 5 | 4.06 | 1.1351 | − | light brown | 4.04 | 1.1353 | − | light brown |

Consequently, these comparative results given from Table 1 to Table 6 demonstrate that the physical stability of the formulation comprising the combination of *Propolis, Ginseng* root and *Zingiber officinale* (Formulation 5) is higher than that of the formulation comprising the combination of *Propolis* and *Ginseng* root (Formulation 4) or of the formulations comprising single extract (Formulation 1, 2, and 3). In other words, use of *Propolis, Ginseng* root and *Zingiber officinale* together in the formulation increases substantially the physical stability of the formulation comprising the combination of *Propolis* and *Ginseng* root. Additionally, the fact that the Formulation 5 has an improved physical stability is also an indication of having an improved chemical stability.

The present invention is further described by the following examples. The purpose of these examples is not to limit the scope of the present invention and should be evaluated in light of the description whose details are given above.

Example 1

Solvents are mixed in the mixer until a homogeneous mixture is obtained. Then, the inactive ingredients are added and mixed until a homogeneous mixture is obtained. Finally,

*Propolis* extract, *Ginseng* root extract and *Zingiber officinale* extract are added, respectively and mixed at high speed until a homogeneous mixture is obtained. The obtained mixture is subjected to the filtering process and let to settle. At the end of the settling period the obtained final product is filled into suitable bottles.

| Ingredients | Amount % |
| --- | --- |
| Propolis extract | 0.02%-5% |
| Ginseng root extract | 0.1%-10% |
| *Zingiber officinale* extract | 0.2%-5% |
| Propylene glycol | 1%-60% |
| Glycerin | 25%-50% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycerizinate | 0.01%-10% |
| Ethanol | 0.5%-30% |
| *Eucalyptus* | 0.01%-5% |
| Water | q.s. | q.s.: Quantity sufficient (enough to complete the total volume of the formulation to 100 ml)

Example 2

Solvents are mixed in the mixer until a homogeneous mixture is obtained. Then, the inactive ingredients are added and mixed until a homogeneous mixture is obtained. Finally, *Propolis* extract, *Ginseng* root extract and *Zingiber officinale* extract are added, respectively and mixed at high speed until a homogeneous mixture is obtained. The obtained mixture is subjected to the filtering process and let to settle. At the end of the settling period the obtained final product is filled into suitable bottles.

| Ingredients | Amount % |
| --- | --- |
| Propolis extract | 0.02%-30% |
| Ginseng root extract | 0.05%-60% |
| *Zingiber officinale* extract | %0.05-%30 |
| Propylene glycol | 10%-30% |
| Glycerin | 25%-50% |
| Citric acid monohydrate | 0.03%-0.2% |
| Sodium citrate dihydrate | %0.015-%0.1 |
| Sorbitol | 10%-25% |
| Sucralose | 0.01%-2% |
| Ammonium glycerizinate | 0.01%-10% |
| Ethanol | 0.5%-30% |
| *Eucalyptus* | 0.05%-2% |
| Water | q.s. | q.s.: Quantity sufficient (enough to complete the total volume of the formulation to 100 ml)

Example 3

Solvents are mixed in the mixer until a homogeneous mixture is obtained. Then, the inactive ingredients are added and mixed until a homogeneous mixture is obtained. Finally, *Propolis* extract, *Ginseng* root extract, *Zingiber officinale* extract and *Glycyrrhiza glabra* extract are added respectively and mixed at high speed until a homogeneous mixture is obtained. The obtained mixture is subjected to the filtering process and let to settle. At the end of the settling period the obtained final product is filled into suitable bottles.

| Ingredients | Amount % |
| --- | --- |
| Propolis extract | 0.02%-5% |
| Ginseng root extract | 0.1%-10% |
| *Zingiber officinale* extract | 0.2%-5% |
| *Glycyrrhiza glabra* extract | 0.1%-4% |
| Propylene glycol | 1%-60% |
| Glycerin | 25%-50% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycerizinate | 0.01%-10% |
| Ethanol | 0.5%-30% |
| *Eucalyptus* | 0.01%-5% |
| Water | q.s. | q.s.: Quantity sufficient (enough to complete the total volume of the formulation to 100 ml)

Example 4

Solvents are mixed in the mixer until a homogeneous mixture is obtained. Then, the inactive ingredients are added and mixed until a homogeneous mixture is obtained. Finally, *Propolis* extract, *Ginseng* root extract, *Zingiber officinale* extract and *Glycyrrhiza glabra* extract are added respectively and mixed at high speed until a homogeneous mixture is obtained. The obtained mixture is subjected to the filtering process and let to settle. At the end of the settling period the obtained final product is filled into suitable bottles.

| Ingredients | Amount % |
| --- | --- |
| Propolis extract | 0.02%-30% |
| Ginseng root extract | 0.05%-60% |
| *Zingiber officinale* extract | 0.05%-30% |
| *Glycyrrhiza glabra* extract | 0.01%-20% |
| Propylene glycol | 10%-30% |
| Glycerin | 25%-50% |
| Citric acid monohydrate | 0.03%-0.2% |
| Sodium citrate dihydrate | 0.015%-0.1% |
| Sorbitol | 10%-25% |
| Sucralose | 0.01%-2% |
| Ammonium glycerizinate | 0.01%-10% |
| Ethanol | 0.5%-30% |
| *Eucalyptus* | 0.05%-2% |
| Water | q.s. | q.s.: Quantity sufficient (enough to complete the total volume of the formulation to 100 ml)

Example 5

Solvents are mixed in the mixer until a homogeneous mixture is obtained. Then, the inactive ingredients are added and mixed until a homogeneous mixture is obtained. Finally, *Propolis* extract, *Ginseng* root extract, *Zingiber officinale* extract and *Glycyrrhiza glabra* extract are added respectively and mixed at high speed until a homogeneous mixture is obtained. The obtained mixture is subjected to the filtering process and let to settle. At the end of the settling period the obtained final product is filled into suitable bottles.

| Ingredients | Amount % |
| --- | --- |
| Propolis extract | 0.02%-5% |
| Ginseng root extract | 0.1%-10% |
| *Zingiber officinale* extract | 0.2%-5% |
| *Glycyrrhiza glabra* extract | 0.1%-4% |
| Propylene glycol | 10%-30% |

-continued

| Ingredients | Amount % |
|---|---|
| Glycerin | 25%-50% |
| Citric acid monohydrate | 0.03%-0.2% |
| Sodium citrate dihydrate | 0.015%-0.1% |
| Sorbitol | 10%-25% |
| Sucralose | 0.01%-2% |
| Ammonium glycerizinate | 0.01%-10% |
| Ethanol | 0.5%-30% |
| Eucalyptus | 0.05%-2% |
| Water | q.s. | q.s.: Quantity sufficient (enough to complete the total volume of the formulation to 100 ml)

Example 6

Solvents are mixed in the mixer until a homogeneous mixture is obtained. Then, the inactive ingredients are added and mixed until a homogeneous mixture is obtained. Finally, Propolis extract, Ginseng root extract, Zingiber officinale extract and Glycyrrhiza glabra extract are added respectively and mixed at high speed until a homogeneous mixture is obtained. The obtained mixture is subjected to the filtering process and let to settle. At the end of the settling period the obtained final product is filled into suitable bottles.

| Ingredients | Amount % |
|---|---|
| Propolis extract | 0.02%-15% |
| Ginseng root extract | 0.05%-25% |
| Zingiber officinale extract | 0.1%-15% |
| Glycyrrhiza glabra extract | 0.05%-10% |
| Propylene glycol | 10%-30% |
| Glycerin | 25%-50% |
| Citric acid monohydrate | 0.03%-0.2% |
| Sodium citrate dihydrate | 0.015%-0.1% |
| Sorbitol | 10%-25% |
| Sucralose | 0.01%-2% |
| Ammonium glycerizinate | 0.01%-10% |
| Ethanol | 0.5%-30% |
| Eucalyptus | 0.05%-2% |
| Water | q.s. | q.s.: Quantity sufficient (enough to complete the total volume of the formulation to 100 ml)

The invention claimed is:

1. A formulation for treating or preventing a respiratory tract disease comprising effective amounts of Propolis extract, Ginseng root extract and Zingiber officinale extract, wherein:
the percentage amount of the Propolis extract based on the total volume of the formulation, is between 0.02% and 30% (w/v);
the percentage amount of the Ginseng root extract based on the total volume of the formulation, is between 0.05% and 60% (w/v);
the percentage amount of the Zingiber officinale extract based on the total volume of the formulation, is less than 30% (w/v); and wherein the formulation further comprises Glycyrrhiza glabra extract.

2. The formulation according to claim 1, wherein the percentage amount of the Zingiber officinale extract based on the total volume of the formulation is less than 15% (w/v), and more preferably between 0.2% and 5% (w/v).

3. The formulation according to claim 1, wherein the percentage amount of the Propolis extract based on the total volume of the formulation, is between 0.02% and 15% (w/v); and more preferably between 0.02% and 5% (w/v).

4. The formulation according to claim 1, wherein the percentage amount of the Ginseng root extract based on the total volume of the formulation, is between 0.05% and 25% (w/v); and more preferably between 0.1% and 10% (w/v).

5. The formulation according to claim 1, wherein the weight ratio of the Glycyrrhiza glabra extract to the Zingiber officinale extract is between 50:1 and 1:20, preferably between 30:1 and 1:10, and more preferably between 20:1 and 1:5.

6. The formulation according to claim 1, wherein said formulation is administered by an oral, parenteral, ocular, nasal, buccal, sublingual or topical route, and the route preferably is oral.

7. The formulation according to claim 6, wherein said route is oral and the formulation is present in a liquid oral dosage form, more preferably in a syrup form.

8. The formulation according to claim 1, further comprising at least one pharmaceutically acceptable excipient selected from the group comprising fillers, solvents, pH adjusting agents, sweeteners, aromatic agents and preservatives.

9. The formulation according to claim 8, wherein the filler is selected from the group comprising sucrose, sorbitol, xylitol, dextrose, fructose, maltitol, sugar potassium, aspartame, saccharin, saccharin sodium, spray dried or anhydrous lactose, mannitol, starch, cellulose (preferably, microcrystalline cellulose) and mixtures thereof, and the filler is preferably sorbitol.

10. The formulation according to claim 9, wherein the filler is sorbitol and the percentage amount of the sorbitol based on the total volume of the formulation is between 1% and 60% (w/v), preferably between 5% and 30% (w/v), and more preferably between 10% and 25% (w/v).

11. The formulation according to claim 8, wherein the pH adjusting agent is selected from the group comprising ascorbic acid, acetic acid, tartaric acid, citric acid, sodium citrate, potassium citrate, sodium phosphate, tricalcium phosphate, calcium carbonate, sodium bicarbonate, calcium phosphates, carbonated calcium phosphates, magnesium hydroxide and hydrates thereof and mixtures thereof, and the pH adjusting agent is preferably citric acid monohydrate and sodium citrate dihydrate.

12. The formulation according to claim 11, wherein the pH adjusting agent is citric acid monohydrate and sodium citrate dihydrate and the weight ratio of the sodium citrate dihydrate to the citric acid monohydrate is 1:2.

13. The formulation according to claim 8, wherein it does not comprise preservatives.

14. The formulation according to claim 8, wherein the aromatic agents are selected from the group comprising fruit aromas such as of orange, cherry, strawberry, banana, cherry, lemon; aromas of cardamom, anise, mint, menthol, eucalyptus, vanillin and ethyl vanillin and mixtures thereof, and the aromatic agent is preferably eucalyptus.

15. The formulation according to claim 14, wherein the aromatic agent is eucalyptus and the percentage amount of the eucalyptus based on the total volume of the formulation is between 0.01% and 5% (w/v), preferably between 0.03% and 3% (w/v), and more preferably between 0.05% and 2%.

16. The formulation according to claim 8, wherein the sweeteners are selected from the group comprising sucralose, ammonium glycerizinate, acesulfame-K, aspartame, saccharin or sodium and calcium salts of saccharin, sodium cyclamate, sucrose, fructose, glucose, sorbitol and mixtures thereof, optionally wherein the percentage amount of the sweetener based on the total volume of the formulation is between 0.005% and 20% (w/v), preferably between 0.005% and 15% (w/v) and more preferably between 0.005% and 10% (w/v).

17. The formulation according to claim 8, wherein the solvents are selected from the group comprising water soluble polar solvents such as propylene glycol, glycerin, water, ethanol, isopropyl alcohol and water insoluble non-polar solvents or a mixture thereof.

18. A method of treating or preventing a respiratory tract disease in a subject in need thereof, or alleviating or eliminating a symptom thereof, the method comprising administering an effective amount of the formulation of claim 1 to the subject.

\* \* \* \* \*